(12) United States Patent
    Ishikawa

(10) Patent No.: US 12,636,414 B2
(45) Date of Patent: May 26, 2026

(54) VALVE MEMBER AND MILKING MACHINE

(71) Applicant: Pigeon Corporation, Chuo-ku (JP)

(72) Inventor: Tatsuyuki Ishikawa, Chuo-ku (JP)

(73) Assignee: Pigeon Corporation, Tokyo (JP)

( * ) Notice: Subject to any disclaimer, the term of this patent is extended or adjusted under 35 U.S.C. 154(b) by 528 days.

(21) Appl. No.: 18/265,632

(22) PCT Filed: Nov. 2, 2021

(86) PCT No.: PCT/JP2021/040439
    § 371 (c)(1),
    (2) Date: Jun. 6, 2023

(87) PCT Pub. No.: WO2022/123964
    PCT Pub. Date: Jun. 16, 2022

(65) Prior Publication Data
    US 2024/0033404 A1    Feb. 1, 2024

(30) Foreign Application Priority Data

Dec. 8, 2020    (JP) ................................. 2020-203094

(51) Int. Cl.
    *A61M 1/06*        (2006.01)
    *A61M 39/24*       (2006.01)
(52) U.S. Cl.
    CPC ............ *A61M 1/062* (2014.02); *A61M 39/24*
    (2013.01); *A61M 2039/2466* (2013.01)
(58) Field of Classification Search
    CPC .................. A61M 1/062; A61M 39/24; A61M
                                        2039/2466
    See application file for complete search history.

(56) References Cited

U.S. PATENT DOCUMENTS 4,857,051 A  *  8/1989  Larsson ................ A61M 1/782
                                                            604/74
5,992,462 A      11/1999  Atkinson et al.
                        (Continued)

FOREIGN PATENT DOCUMENTS

CN          101232909          7/2008
CN          306688637          7/2021
                    (Continued)

OTHER PUBLICATIONS

"Chinese Application Serial No. 202180080795.X, First Office Action mailed Jul. 4, 2025", w/ English translation, 20 pgs.
                    (Continued)

*Primary Examiner* — Dung T Ulsh
(74) *Attorney, Agent, or Firm* — Schwegman Lundberg & Woessner, P.A.

(57)            ABSTRACT

Provided are a valve member and a milking machine that are easy to wash. The valve member enables an internal passage to temporarily retain milk when the milking machine is in a negative pressure state, and enables the milk retained in the internal passage to be discharged when the milking machine is in a normal pressure state. The valve member is provided with a cap that is attached to the milking machine. The cap is provided with a partition wall that separates a first space on the milk inflow side and a second space on the milk outflow side. A through hole in the partition wall allows communication between the first space and the second space. A valve body disposed in the second space closes the through hole when the negative pressure state is established, and opens the through hole when the normal pressure state is established.

18 Claims, 7 Drawing Sheets

(56) References Cited

U.S. PATENT DOCUMENTS

| | | | |
|---|---|---|---|
| 6,270,474 | B1 | 8/2001 | Nueesch |
| D479,876 | S | 9/2003 | Gradon et al. |
| D580,048 | S | 11/2008 | Guney et al. |
| D581,041 | S | 11/2008 | Moore et al. |
| D591,856 | S | 5/2009 | Lulla et al. |
| D597,658 | S | 8/2009 | Fisher et al. |
| D610,250 | S | 2/2010 | Neuner |
| D679,376 | S | 4/2013 | Von et al. |
| D720,466 | S | 12/2014 | Edding |
| D754,327 | S | 4/2016 | Row |
| D811,580 | S | 2/2018 | Tang et al. |
| D820,973 | S | 6/2018 | Albert |
| D831,198 | S | 10/2018 | Ross et al. |
| D882,062 | S | 4/2020 | Brown |
| D886,985 | S | 6/2020 | Subbanna et al. |
| D898,184 | S | 10/2020 | Miller |
| D922,572 | S | 6/2021 | Bertrand et al. |
| D930,816 | S | 9/2021 | Zhang |
| D941,460 | S | 1/2022 | Zhang |
| 11,298,445 | B2 | 4/2022 | Analytis et al. |
| D955,551 | S | 6/2022 | Sanders |
| 2007/0078383 | A1 | 4/2007 | Tashiro et al. |
| 2007/0173756 | A1 | 7/2007 | Krebs et al. |
| 2016/0038662 | A1 | 2/2016 | Felber |
| 2019/0143014 | A1* | 5/2019 | Ochiai .................... A61M 1/82 |
| | | | 604/74 |
| 2020/0289729 | A1 | 9/2020 | Van Asseldonk et al. |

FOREIGN PATENT DOCUMENTS

| | | |
|---|---|---|
| GB | 6169539 | 10/2022 |
| JP | S61252980 A | 11/1986 |
| JP | 2009228812 A | 10/2009 |
| JP | 4486681 B2 | 4/2010 |
| JP | 2015152144 A | 8/2015 |

OTHER PUBLICATIONS

European Application No. 21903068.1, Extended Search Report, mailed Oct. 11, 2024, 9 pgs.

"Chinese Application Serial No. 2021800807975.X, First Office Action mailed Jul. 4, 2025", w/ English translation, 20 pgs.

"Chinese Application Serial No. 2021800807975, First Office Action mailed Jul. 4, 2025", w/ English translation, 20 pgs.

International Application No. PCT/JP2021/040439, International Search Report mailed Dec. 28, 2021 (2 pgs.).

"Maymom Replacement Parts 2 Diaphragm and 2 Duckbill for Avent Comfort Electric Pumps,", Maymom, Amazon.com, [Post-date: Sep. 30, 2016], [Site seen Dec. 28, 2022], Seen at URL: https://www.amazon.in/Maymom-Replacement-Parts-Comfort-Electric/dp/B01CCBMSYK, (2016) (2 pgs.).

"Pigeon Milk Valve for Electric Breast Pump (2 Piece).", Pigeon Corp, Amazon.com, [Postdate: Jan. 23, 2015], [Site seen Dec. 28, 2022], Seen at URL: https://www.amazon.in/Pigeon-Valve-Electric-Breast-Piece/dp/BOOSMZ2KHG, (2015) (2 pgs.).

* cited by examiner

VALVE MEMBER AND MILKING MACHINE

This application is a U.S. National Stage Filing under 35 U.S.C. 371 from International Application No. PCT/JP2021/040439, filed on Dec. 11, 2021, and published as WO 2022/123964 A1 on Jun. 16, 2022, which claims the benefit of priority under 35 U.S.C. § 119 to Japanese Patent Application No. 2020-203094, each of which is incorporated by reference herein in its entirety.

TECHNICAL FIELD

The present disclosure relates to a valve member and a breast pump including a valve member.

BACKGROUND ART

Patent Literature 1, for example, describes that a manual breast pump has a main body, to which a hood to be applied to a breast and a bottle for storing milk are attached. The breast pump further includes a diaphragm that creates a negative pressure in an internal passage that connects the milk extraction opening defined by the hood to the bottle, and a handle for displacing the diaphragm by manual operation. In the breast pump, the volume of the internal passage increases when the diaphragm is displaced upward by operating the handle. This creates a negative pressure in the internal passage. While a negative pressure is created, the milk expressed from the nipple is stored in the internal passage. When the internal passage returns from a negative pressure state to a normal pressure state, the valve in the internal passage opens to allow the milk to flow into the bottle.

A valve member is attached to the lower end of the internal passage for temporarily storing the milk in the internal passage before discharging it into the bottle. The valve member is a molded member of an elastic synthetic resin such as silicone rubber. The valve member has a base attached to the lower end of the internal passage and two planar movable portions extending from the lower end of the base. The two planar movable portions are arranged such that the distance between them gradually decreases toward the distal ends. A slit is formed in the section in which the distal ends of the two planar movable portions are placed against each other. The valve member is configured such that the elasticity of the planar movable portions automatically closes the slit.

CITATION LIST

Patent Literature

Patent Literature 1: Japanese Laid-Open Patent Publication No. 2015-152144

SUMMARY OF INVENTION

Technical Problem

With such a breast pump, the valve member for causing the milk stored in the internal passage to flow out into the bottle needs to be easy to clean in order to maintain the cleanliness of the breast pump. However, the base of the valve member described in the above publication is tubular, and the valve body of the valve member has a triangular cross-section. Thus, the inner surface of the valve member has a shape that is difficult to clean.

Cleanliness is required not only for manual breast pumps, but also for electric breast pumps. A valve member used in an electric breast pump also needs to be easy to clean.

Solution to Problem

One aspect of the present disclosure provides a valve member for a breast pump. The valve member is configured to allow milk to be temporarily stored in an internal passage when the breast pump is in a negative pressure state, and to allow the milk stored in the internal passage to flow out when the breast pump is in a normal pressure state. The valve member includes a cap configured to be attached to the breast pump. The cap includes a partition wall and a through-hole. The partition wall separates a first space on an inflow side of the milk from a second space on an outflow side of the milk. The through-hole is disposed in the partition wall to connect the first space to the second space. The valve member includes a valve body disposed in the second space. The valve body is configured to close the through-hole when the negative pressure state is created, and to open the through-hole when the normal pressure state is established.

According to the above configuration, during milk extraction, the internal passage is brought into a negative pressure state, causing the valve body in the second space to be lifted toward the first space, comes into close contact with the partition wall, and thus closes the through-hole. The milk is therefore temporarily stored in the first space. When the internal passage is brought into a normal pressure state, the valve body is separated from the partition wall, and the milk in the first space flows out to the second space through the through-hole. This valve member can be easily cleaned by removing the valve body from the cap.

In the above valve member, the valve body may include a plate-shaped portion for closing the through-hole, and an attachment projection extending from the plate-shaped portion. The partition wall may be configured to include an attachment hole that is engaged with the attachment projection. According to the above configuration, the operation of attaching or detaching the valve body with respect to the cap only involves attachment or detachment of the connection projection with respect to the attachment hole, and is thus easy.

In the above valve member, a cap may include an outer circumference wall, and a portion of the outer circumference wall defining the second space may include a thick section that has a first thickness and bulges inward and a thin section that is thinner than the thick section and has a second thickness. According to the above configuration, the milk flowing out through the through-hole into the second space is received by the plate-shaped portion of the valve body and then flows toward the outer circumference wall. The distance between the outer circumference edge of the valve body and the inner side of the outer circumference wall is wider at a position corresponding to the thin section than at a position corresponding to the thick section. Thus, the milk received by the plate-shaped portion tends to flow into the storage container at a position corresponding to the thin section. Some of the milk is transmitted from the outer circumference edge of the valve body to the thick section and the thin section and flows into the storage container from the distal end of the outer circumference wall. In this manner, the flow of some of the milk is conditioned and moves into the storage container from the distal end of the portion of the outer circumference wall defining the second space. Thus, as compared to a configuration in which the milk is scattered into the bottle, the dripping sound of milk is reduced.

In the valve member described above, the portion of the outer circumference wall defining the second space may include a high section that has a first height as a height from the partition wall, and a low section that has a second height as a height from the partition wall. The second height is lower than the first height. The thick sections may be formed in the low section, and the thin section may be formed in the high section. According to the above configuration, some of the milk is guided from the low section of the thick section to the high section of the thin section, and flows into the storage container from the distal end of the high section.

In the above valve member, the through-hole may be one of a plurality of through-holes arranged in the partition wall in a circumferential direction. The partition wall may include a central region inward of the through-holes, an outer circumference region radially outward of the through-holes, and a plurality of connection sections disposed between adjacent ones of the through-holes to connect the central region to the outer circumference region. In the portion of the outer circumference wall defining the second space, the thick section may be disposed at a position corresponding to one of the connection sections, and the thin section may be disposed at a position corresponding to one of the through-holes.

According to the above configuration, while the milk flowing into the second space through the through-holes flows toward the outer circumference wall after being received on the surface of the valve body, the milk flows evenly in all directions without being biased in a particular direction. At the thin section formed at a position corresponding to a through-hole, a space is formed that is wider than a space formed at the thick section formed at a position corresponding to a connection section. As such, some of the milk flowing out through the through-holes tends to flow along the thin section. Some of the milk is transferred from the outer circumference edge of the valve body to the thick section and the thin section and flows into the storage container from the distal end of the outer circumference wall.

In the above valve member, the valve body may be a molded product of an elastic synthetic resin material. According to the above configuration, a negative pressure state of the temporary storage portion brings the valve body into close contact with the partition wall, so that the through-hole is firmly closed.

In the above valve member, the valve body may include a plate-shaped portion for closing the through-hole, and the plate-shaped portion may have a facing surface that faces the partition wall and is frosted. According to the above configuration, the facing surface facing the partition wall is unlikely to stick to the partition wall.

Another aspect of the present disclosure provides a breast pump including: a storage container configured to store milk; a hood configured to be applied to a breast; an internal passage configured to temporarily store expressed milk and to connect a milk extraction opening defined by the hood to the storage container; and a valve member configured to cause the milk temporarily stored in the internal passage to flow out to the storage container. The valve member has a configuration as described above. The breast pump further includes a negative pressure creation mechanism configured to alternately create a negative pressure state and a normal pressure state in the internal passage. In the above breast pump, the valve member is configured to allow milk from the hood to be temporarily stored in the internal passage when the breast pump is in the negative pressure state, and to allow the milk stored in the internal passage to flow out to the storage container when the breast pump is in the normal pressure state.

Advantageous Effects of Invention

The present disclosure facilitates cleaning of a valve member.

DESCRIPTION OF EMBODIMENTS

Referring to FIGS. 1 to 10, a breast pump is now described.

Figure 1:
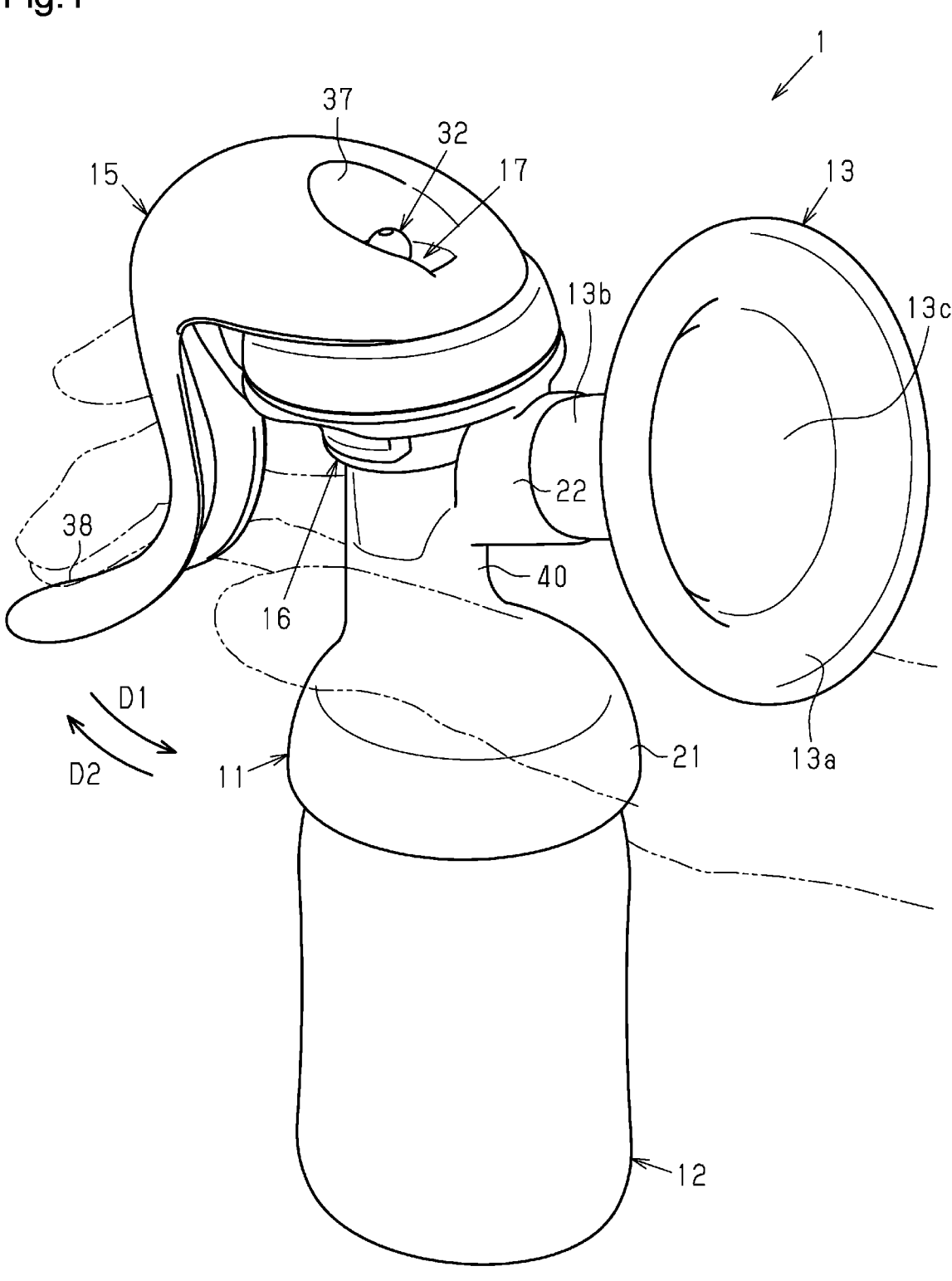
FIG. 1 is a perspective view of a breast pump.

As shown in FIG. 1, a breast pump 1 is a manual breast pump sized to be operated with one hand by a user. The breast pump 1 includes a main body 11, a bottle 12, a hood 13, a diaphragm 14 (see FIG. 2), a handle 15, a handle base 16, and a lift plate 17.

The bottle 12, which serves as a storage container for storing milk, is connected to the main body 11. The main body 11 is a member to which the hood 13, which is to be applied to a breast, is attached. The main body 11 is a molded product made of a lightweight, hard synthetic resin material. Specifically, the main body 11 is made of a synthetic resin material such as polypropylene or polycarbonate.

Figure 2:
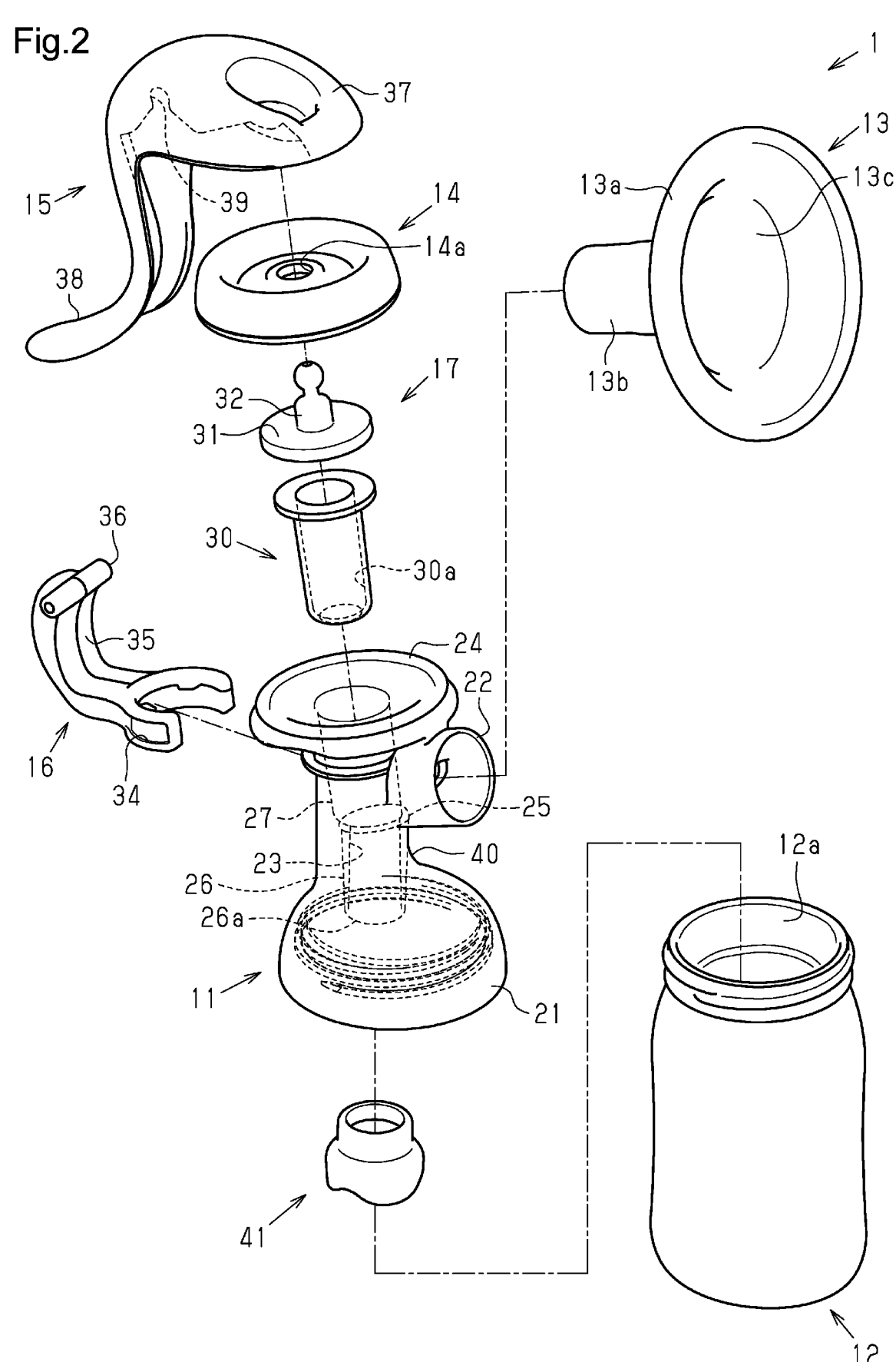
FIG. 2 is an exploded perspective view of the breast pump shown in FIG. 1.

As shown in FIG. 2, the main body 11 includes a bottle attachment portion 21, a hood attachment portion 22, and the internal passage 23. The bottle attachment portion 21 is positioned below the hood attachment portion 22. The bottle 12 is a container for storing milk. The bottle 12 has a bottle opening 12a to be connected to the bottle attachment portion 21. Instead of the main body 11, an artificial nipple may be attached to the bottle opening 12a. This allows the bottle 12 to serve as a container of a baby bottle. To allow the bottle attachment portion 21 to close the bottle opening 12a, the inner surface of the bottle attachment portion 21 has a thread section, which may be threadedly engaged with the thread section on the outer surface of the circumferential wall defining the bottle opening 12a to be fastened.

The hood attachment portion 22 is tubular and includes an inflow passage 25 connected to the internal passage 23. The hood 13 includes an increasing diameter portion 13a, which is to be applied to a breast and dome-shaped or trumpet-shaped corresponding to the shape of the breast, and a tubular portion 13b, which is located at the apex of the increasing diameter portion 13a. The increasing diameter portion 13a has a milk extraction opening 13c on its inner side. An elastic pad or the like is attached to the outer edge, which is the open end, of the increasing diameter portion 13a. This helps to achieve close contact between the open end of the increasing diameter portion 13a and the breast. The tubular portion 13b is inserted and fitted into the hood attachment portion 22.

The internal passage 23 is provided inside the main body 11. The internal passage 23 extends between the lower end 26a, which is located inward of the bottle attachment portion 21, and an attachment end 24, to which the diaphragm 14 is attached, and thus connects the lower end 26a to the attachment end 24. The internal passage 23 also includes the outlet of the inflow passage 25 between the attachment end 24 of the internal passage 23 and the lower end 26a of the internal passage 23 inward of the bottle attachment portion 21. In the internal passage 23, the passage between the outlet of the inflow passage 25 and the lower end 26a, which is inward of the bottle attachment portion 21, functions as a temporary storage portion 26, which temporarily stores the milk flowing from the hood 13. Also, in the internal passage 23, the passage from the attachment end 24 to the inflow passage 25 functions as a negative pressure creation passage 27, in which a negative pressure is created. The upper end of the negative pressure creation passage 27 is the attachment end 24, to which the diaphragm 14 is attached. The attachment end 24 has the shape of a flange widening outward, thereby increasing the opening area of the internal passage 23.

The diaphragm 14 functions as a negative pressure creation member, which creates a negative pressure in the internal passage 23. The diaphragm 14 is a molded product of a synthetic resin material having flexibility and elasticity, such as silicone rubber, for example. The diaphragm 14 is retained to block the attachment end 24. The inflow passage 25 and the internal passage 23 connect the lower end 26a of the temporary storage portion 26 to the milk extraction opening 13c. When the hood 13 is applied to the breast and the milk extraction opening 13c is closed by the breast with the internal passage 23 and the inflow passage 25 closed by the valve member 41 and the diaphragm 14, the internal passage 23 and the inflow passage 25 form a space that is substantially sealed. The lift plate 17, as a connection portion for connection to a handle 15, is provided in diaphragm 14.

The lift plate 17 is a molded member made of a synthetic resin material harder than the diaphragm 14, such as a molded product made of an elastic synthetic resin material such as polycarbonate. The lift plate 17 serves as the connection portion with the handle 15. The lift plate 17 includes a plate portion 31 and a connection projection 32. The plate portion 31 is positioned on the inner surface of the diaphragm 14 (the lower surface as viewed in FIG. 2). The connection projection 32 extends from a central portion of the surface of the plate portion 31 facing the diaphragm 14. The center portion of the diaphragm 14 includes an insertion hole 14a, and the connection projection 32 extends outward (upward in FIG. 2) of the diaphragm 14 through the insertion hole 14a.

A tubular insertion member 30 is attached to the plate portion 31. The insertion member 30 includes an insertion portion 30a, which is inserted in the portion of the internal passage 23 serving as the negative pressure creation passage 27. The insertion portion 30a reduces the volume of the negative pressure creation passage 27, which is a part of the internal passage 23. The insertion portion 30a extends in a shape that corresponds to the internal shape of the negative pressure creation passage 27 of the internal passage 23. That is, the insertion portion 30a is tubular and inserted into the negative pressure creation passage 27 along the inner circumference surface of the negative pressure creation passage 27. The insertion portion 30a reduces the volume of the negative pressure creation passage 27 by reducing the diameter of the internal space of the negative pressure creation passage 27. The insertion portion 30a has a length that does not block the outlet of the inflow passage 25, which is connected to the temporary storage portion 26, when the diaphragm 14 is lifted. This allows the milk to flow from the inflow passage 25 into the temporary storage portion 26 when a negative pressure is created in the temporary storage portion 26.

The handle 15 is supported by a handle base 16 so as to be rotatable relative to the main body 11. The handle base 16 is rotationally attached to a tubular base portion of the attachment end 24. The handle base 16 has an attachment portion 34 and a rotation support piece 35. The attachment portion 34 is C-shaped and fitted to the base portion of the attachment end 24. The handle base 16 thus attached to the attachment end 24 is rotatable in the circumferential direction relative to the attachment end 24. The rotation support piece 35 is a curved extension piece extending upward from the attachment portion 34. The distal end portion of the rotation support piece 35 is located above the diaphragm 14. The distal end portion of the rotation support piece 35 includes a support shaft portion 36 serving as a rotation shaft portion for rotationally supporting the handle 15.

The handle 15 is made of a synthetic resin material such as polycarbonate. The handle 15 includes a lift portion 37 and a lever portion 38. The lift portion 37 is a section for lifting the diaphragm 14 through the lift plate 17. The connection projection 32 of the lift plate 17 is engaged with the lift portion 37. This allows the handle 15 to lift the diaphragm 14.

The lever portion 38 functions as a handle. The lever portion 38 extends from the lift portion 37 to the lower side in which the bottle 12 is to be placed. The handle 15 includes a bearing portion 39 on the inner side of the boundary between the lever portion 38 and the lift portion 37. The support shaft portion 36 is engaged with this bearing portion 39. The support shaft portion 36 is rotationally engaged with the bearing portion 39. The handle 15 thus supported is rotational relative to the main body 11. The handle 15 reciprocates with the bearing portion 39 as the rotation fulcrum. A force applied by the hand rotates the handle 15 in the direction of arrow D1 (FIG. 1), which is the rotational operation direction toward the main body 11 and the bottle 12. The elastic restoring force of the diaphragm 14 rotates the handle 15 in the direction of arrow D2 (FIG. 1), which is the returning direction away from the main body 11 and the bottle 12.

As shown in FIG. 1, the main body 11 includes a recess 40 under the hood attachment portion 22 of the main body 11, which is opposed to the handle 15. The recess 40 is engaged by the base of the user's thumb. That is, the user of the breast pump 1 places fingers other than the thumb on the lever portion 38 and engages with the recess 40 with the base of the thumb to perform an action of grabbing the breast pump 1 with the palm. This provides rotational operation of the handle 15 with the support shaft portion 36 as the fulcrum.

Figure 3:
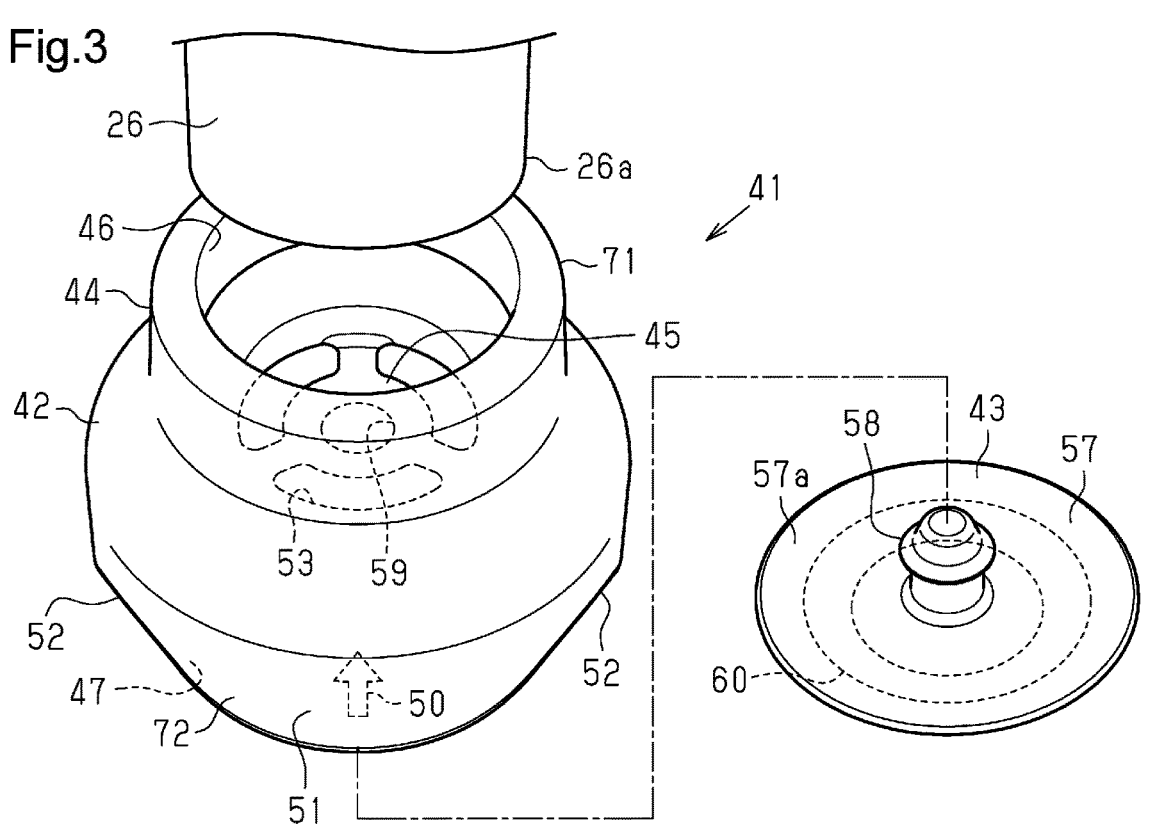
FIG. 3 is an exploded perspective view of a valve member shown in FIG. 2.

As shown in FIG. 2, the lower end 26a of the internal passage 23, that is, the lower end 26a of the temporary storage portion 26 faces the bottle opening 12a when the bottle 12 is attached to the bottle attachment portion 21. As shown in FIGS. 2 and 3, the valve member 41 for the breast pump 1 is attached to the lower end 26a of the internal passage 23. The valve member 41 is positioned inside the bottle opening 12a. The valve member 41 is a check valve. That is, the valve member 41 prevents milk and air in the bottle 12 from flowing back to the main body 11. Also, the valve member 41 separates the internal passage 23 from the internal space of the bottle 12, thereby allowing a negative pressure state to be created in the internal passage 23. The diaphragm 14, the handle 15, and the lift plate 17 form a negative pressure creation mechanism, which alternately creates a negative pressure state and a normal pressure state in the internal passage 23.

As shown in FIG. 3, the valve member 41 includes a cap 42, which is to be attached to the lower end 26a of the internal passage 23, that is, the lower end 26a of the temporary storage portion 26, and a valve body 43, which is placed in the cap 42. The cap 42 and the valve body 43 are molded products of an elastic synthetic resin material such as silicone rubber. As shown in FIG. 3, the cap 42 includes a tubular outer circumference wall 44 and a partition wall 45 extending inward from the outer circumference wall 44. The partition wall 45 divides the internal space in the outer circumference wall 44 into two spaces of an upper space and a lower space in the height direction of the outer circumference wall 44 (the up-down direction as viewed in FIGS. 2 and 3). The partition wall 45 defines a first space 46 as the upper space on the side corresponding to the temporary storage portion 26 and a second space 47 as the lower space on the side corresponding to the bottle 12. The first space 46 is connected to the internal passage 23. The partition wall 45 partitions the internal space of the cap 42 into the first space 46 on the inflow side of the milk and the second space 47 on the outflow side of the milk. The outer circumference wall 44 includes a first outer circumference wall 71 and a second outer circumference wall 72. The first outer circumference wall 71 is the portion of the outer circumference wall 44 that defines the first space 46. The second outer circumference wall 72 is the portion of the outer circumference wall 44 that defines the second space 47.

Figure 4:
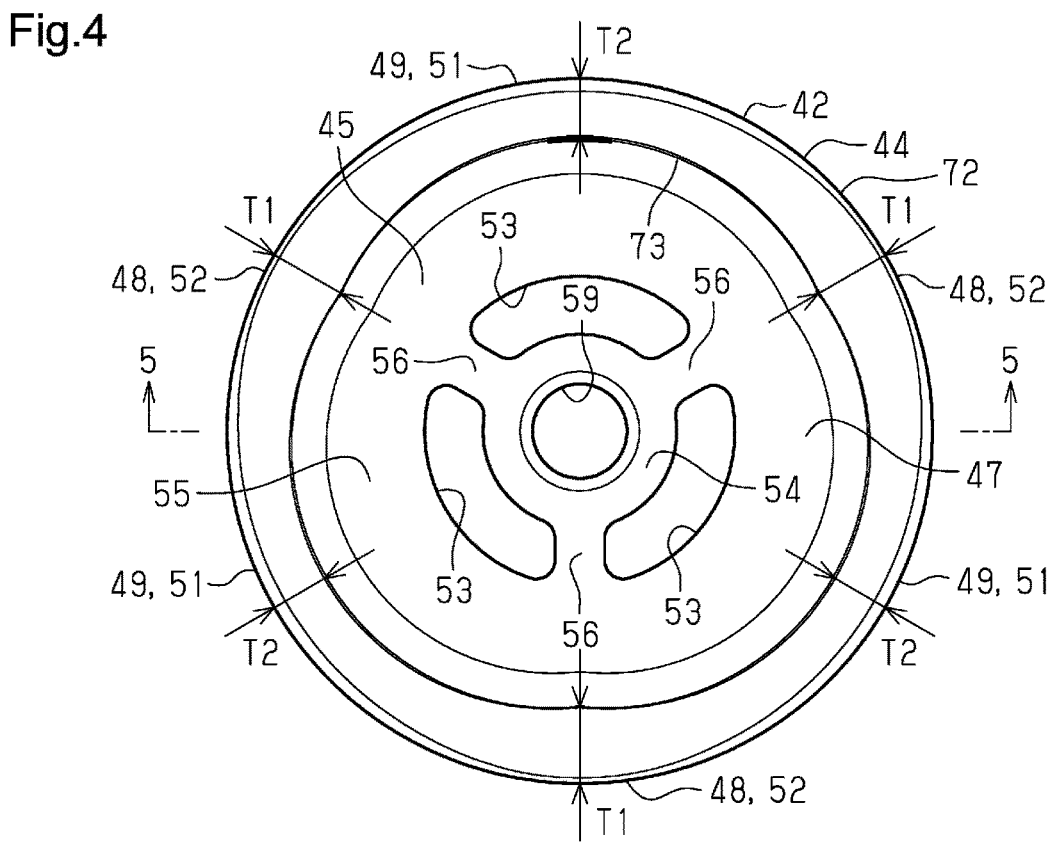
FIG. 4 is a bottom view of a cap shown in FIG. 3.
Figure 5:
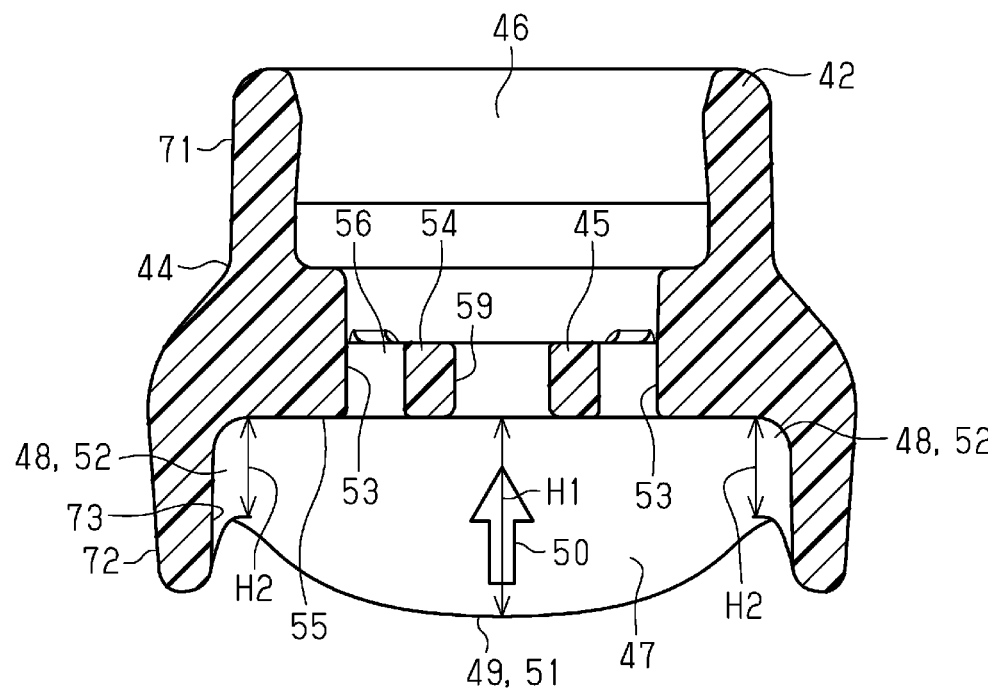
FIG. 5 is a cross-sectional view taken along line 5-5 of FIG. 4.

As shown in FIG. 3, the inner diameter of the first outer circumference wall 71, which defines the first space 46, is sized to allow the outer circumference wall 44 to be fitted over the tubular portion defining the lower end 26a of the internal passage 23. As shown in FIG. 5, the second outer circumference wall 72, which defines the second space 47, has a larger inner diameter than the first space 46 and is wider than the first outer circumference wall 71, which defines the first space 46. As shown in FIG. 4, the second outer circumference wall 72, which defines the second space 47, has multiple thick sections 48 having a first thickness T1 and multiple thin sections 49 having a second thickness T2 that is less than the first thickness T1. Three thick sections 48 and three thin sections 49 are provided alternately in the circumferential direction along the inner circumference surface of the second outer circumference wall 72 defining the second space 47. On the inner circumference surface of the second outer circumference wall 72 defining the second space 47, the thick sections 48 protrude radially inward relative to the thin sections 49, while the thin sections 49 are recessed relative to the thick sections 48. On the inner circumference surface of the second outer circumference wall 72 defining the second space 47, gently curved surfaces connect the thinnest parts of the thin sections 49 to the thickest parts of the thick sections 48 and connect the thickest parts of the thick sections 48 to the thinnest parts of the thin sections 49.

As shown in FIG. 5, the lower end of the second outer circumference wall 72 defining the second space 47 includes alternating high sections 51 and low sections 52. The high sections 51 have a first height H1, which is a distance (height) from the partition wall 45. The low sections 52 have a second height H2, which is less than the first height H1. Three high sections 51 and three low sections 52 are provided alternately in the circumferential direction. Also, gentle curves connect the highest parts of the high sections 51 (the lowest parts of the lower end of the outer circumference wall 44 as viewed in FIG. 5) and the lowest parts of the low sections 52 (the uppermost parts of the lower end of the outer circumference wall 44 as viewed in FIG. 5). That is, the distal end (lower end) of the second outer circumference wall 72 defining the second space 47 has a corrugated shape with two heights of the highest parts and the lowest parts. The high sections 51 are provided at the positions of the thin sections 49, and the low sections 52 are provided at the positions of the thick sections 48. The first height H1 is the height (dimension in the up-down direction) from the surface of the partition wall 45 defining the second space 47 to the highest parts of the high sections 51 (the lowest parts of the lower end of the outer circumference wall 44 as viewed in FIG. 5). The second height H2 is the height from the surface of the partition wall 45 defining the second space 47 to the lowest parts of low sections 52 (the uppermost parts of the lower end of the outer circumference wall 44 as viewed in FIG. 5).

The inner surface of each high section 51 defining the second space 47 (the surface facing radially inward) has a larger area than the inner surface of a low section 52. The inner surface of the high section 51 includes an attachment direction indication portion 50. The attachment direction indication portion 50 indicates the attachment direction for fitting the first space 46 of the valve member 41 over the lower end 26a of the temporary storage portion 26 and the attachment direction for attaching the valve body 43 to the partition wall 45. In one example, the attachment direction indication portion 50 may be an arrow and formed by lines protruding from the inner surface of the high section 51.

As shown in FIG. 4, the partition wall 45 includes multiple through-holes 53 between its center and the inner circumference surface of the outer circumference wall 44 (the outer edge of the partition wall 45). The number of through-holes 53 is three, and these through-holes 53 are provided at regular intervals. That is, the through-holes 53 are arranged in the partition wall 45 in the circumferential direction. Each through-hole 53 is an elongated hole having an arcuate shape extending in the circumferential direction. The partition wall 45 includes a central region 54 inward (radially inward) of the through-holes 53 and an outer circumference region 55 outward of the through-holes 53 as seen from the side of the second space 47 (from below). The outer circumference region 55 is a region between the through-holes 53 and the inner circumference surface of the outer circumference wall 44. The partition wall 45 also includes multiple connection sections 56 located between adjacent through-holes 53. The connection sections 56 connect the central region 54 to the outer circumference region 55. The thickest parts of the thick sections 48 and the lowest parts of the low sections 52 are provided at positions corresponding to the connection sections 56, and the thinnest parts of the thin sections 49 and the highest parts of the high sections 51 are provided at positions corresponding to the through-holes 53. The highest part of each high section 51 and the thinnest part of the corresponding thin section 49 are located between two radially extending lines connecting the center of the partition wall 45 and the opposite longitudinal ends of the corresponding through-hole 53. An attachment hole 59 for attaching the valve body 43 is provided at the center of the central region 54, that is, at the center of the partition wall 45.

Figure 6:
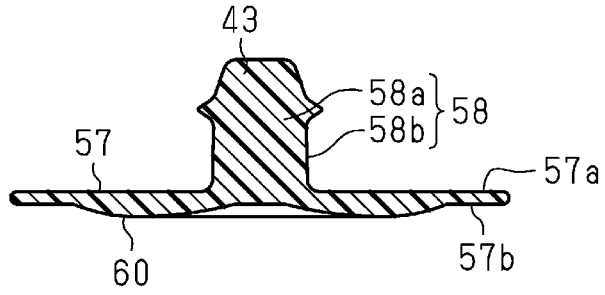
FIG. 6 is a cross-sectional view of a valve body shown in FIG. 3.
Figures 8, 9:
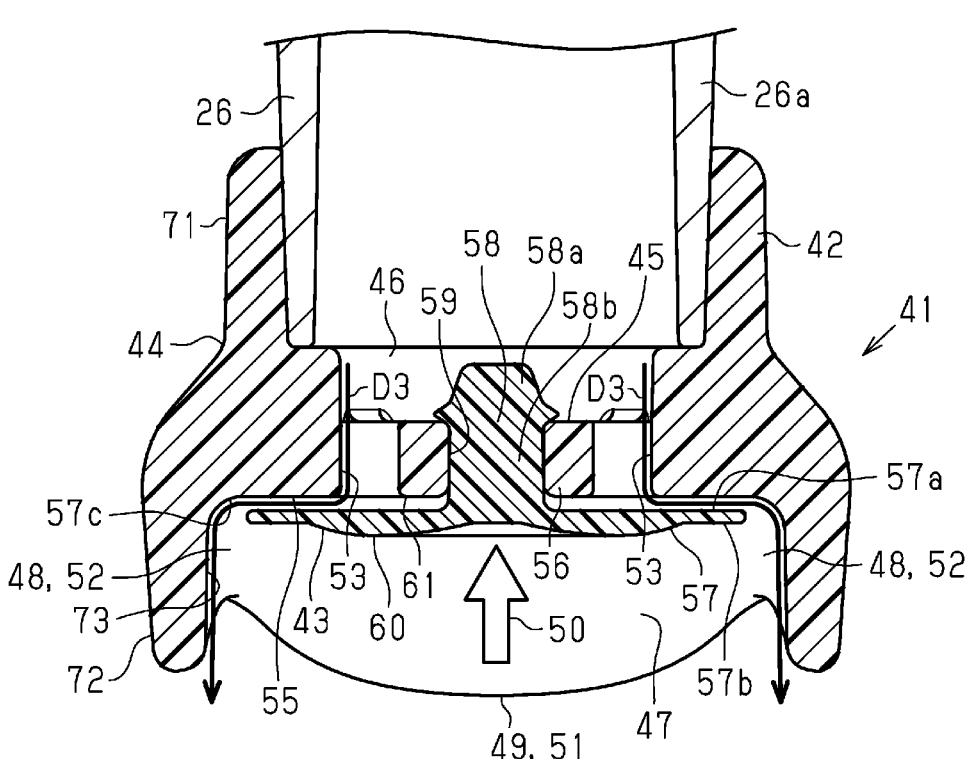
FIG. 8 is a cross-sectional view of the valve member in a situation in which the internal passage of the breast pump shown in FIG. 7 is in a normal pressure state.
FIG. 9 is a cross-sectional view of the valve member in a situation in which the internal passage of the breast pump shown in FIG. 7 is in a negative pressure state.

As shown in FIG. 6, the valve body 43 includes a plate-shaped portion 57 for blocking the through-holes 53 and an attachment projection 58 extending from the plate-shaped portion 57. The plate-shaped portion 57 has a first surface 57a facing the partition wall 45 and a second surface 57b facing the second space 47 on the side opposite to the first surface 57a. The plate-shaped portion 57 is dimensioned to be placed in the second outer circumference wall 72 defining the second space 47 and has the shape of a circular plate in this example. As shown in FIG. 8, the plate-shaped portion 57 is dimensioned to define a slight gap 57c (see FIG. 8) between the outer circumference edge of the plate-shaped portion 57 and the inner surface (inner circumference surface) 73 of the second outer circumference wall 72 defining the second space 47. This gap 57c is a gap through which the milk flows.

As shown in FIG. 6, the first surface 57a is flat in shape, while the second surface 57b includes an annular protrusion 60 (FIG. 3) connecting the positions corresponding to the through-holes 53. The annular protrusion 60 increases the thickness of the plate-shaped portion 57 and thus limits deformation of the plate-shaped portion 57. The first surface 57a is a facing surface facing the partition wall 45. The first surface 57a is frosted and has minute projections and depressions. The frosted first surface 57a is unlikely to stick to the partition wall 45.

The attachment projection 58 is provided in the center of the first surface 57a. The attachment projection 58 includes an annular bulging portion 58a at its distal end and thus includes a retaining groove 58b at the base of the bulging portion 58a. When the attachment projection 58 in the second space 47 is press-fitted into the first space 46 from the second space 47, the circumference edge defining the attachment hole 59 is retained in the retaining groove 58b.

The plate-shaped portion 57 is positioned adjacent to but separated from the partition wall 45 in the second space 47. When the valve body 43 is attached to the cap 42, a space is formed in the second space 47 between the outer circumference edge of the plate-shaped portion 57 and the inner surface (inner circumference surface) 73 of the second outer circumference wall 72 defining the second space 47. This space is wider at positions corresponding to the thin sections 49 than at positions corresponding to thick sections 48. That is, between the outer circumference edge of the plate-shaped portion 57 and the inner surface (inner circumference surface) 73 of the second outer circumference wall 72 defining the second space 47, a space is defined that is wider at positions corresponding to the through-holes 53 than at positions corresponding to the connection sections 56.

Operation of the breast pump 1 configured as above is now described.

The breast pump 1 in a disassembled state is assembled as follows.

Initially, the cap 42 and the valve body 43 of the valve member 41 are separated from each other. To assemble the valve member 41, referring to the attachment direction indication portion 50, the valve body 43 is inserted into the second space 47 of the cap 42 with the attachment projection 58 facing the partition wall 45. That is, it is possible to prevent the user from erroneously inserting the cap 42 into the first space 46. When the attachment projection 58 is inserted in the attachment hole 59, the circumference edge of the partition wall 45 defining the attachment hole 59 is retained in the retaining groove 58b. The cap 42 of the valve member 41 is thus integrated with the valve body 43. Then, the first space 46 of the cap 42 is fitted over the lower end 26a of the temporary storage portion 26. The cap 42 is a molded product made of an elastic synthetic resin material and is thus brought into close contact with the lower end 26a. At this time, the user can easily identify the attachment direction of the valve member 41 relative to the lower end 26a by looking at the attachment direction indication portion 50.

Also, the lift plate 17 and the insertion member 30 are integrated, and the insertion portion 30a is inserted into the negative pressure creation passage 27. Then, the connection projection 32 is inserted through the insertion hole 14a of the diaphragm 14, and the diaphragm 14 is attached to the attachment end 24. The handle base 16 is attached to the main body 11. The connection projection 32 is engaged with the lift portion 37 of the handle 15. Also, the support shaft portion 36 of the handle base 16 is engaged with the bearing portion 39 of the handle 15. Furthermore, the bottle 12 is attached to the bottle attachment portion 21 of the main body 11, and the hood 13 is attached to the hood attachment portion 22.

Figure 7:
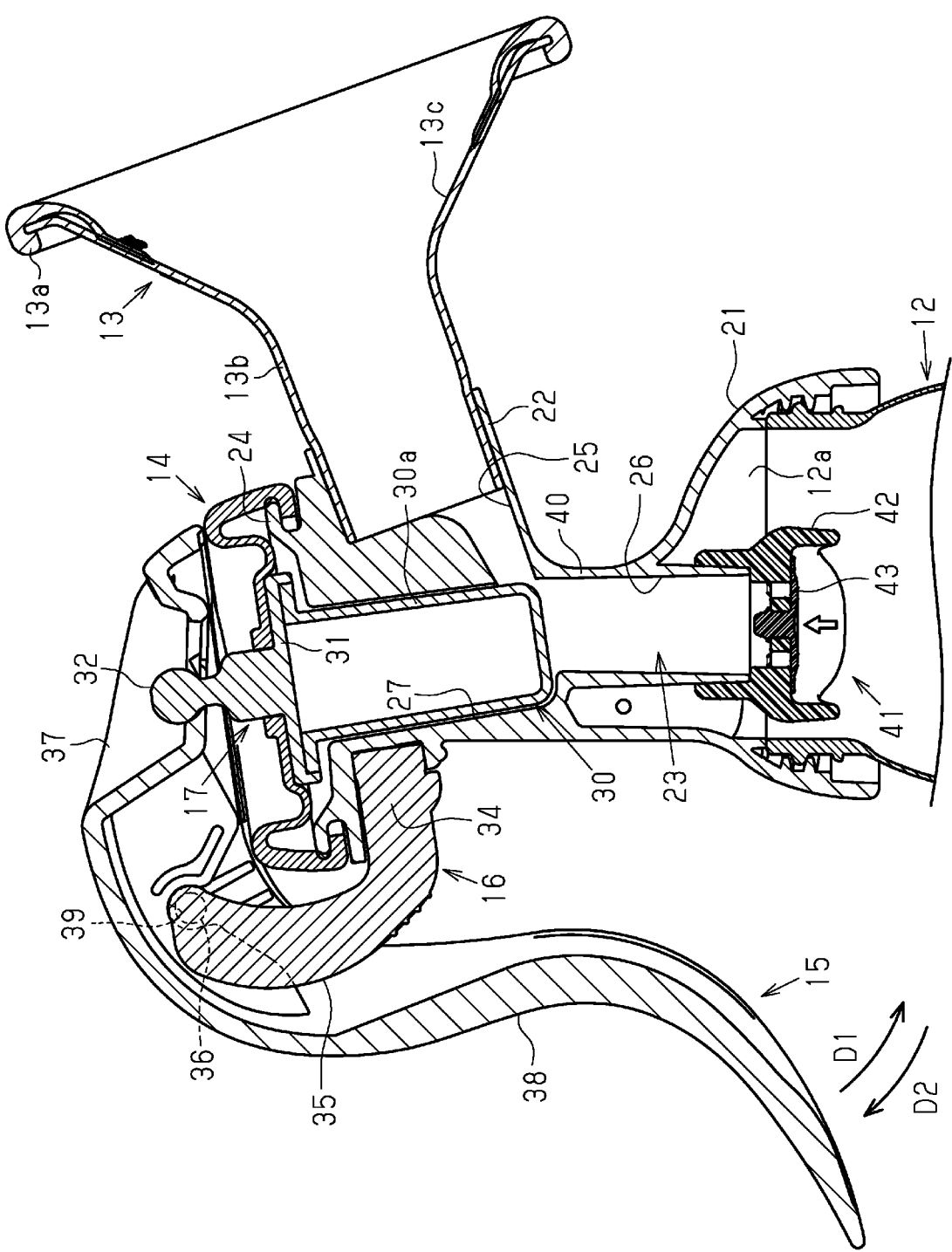
FIG. 7 is a cross-sectional view of the breast pump shown in FIG. 1 in a situation in which the internal passage of the breast pump is in a normal pressure state.

As shown in FIG. 7, to extract milk, the user holds the breast pump 1 and applies the hood 13 to the breast of the user so that the milk extraction opening 13c is closed. This defines, within the internal passage 23, a space that is substantially sealed.

When the handle 15 is manually rotated in the direction of arrow D1 that moves the lever portion 38 closer to the side surface of the bottle 12, the diaphragm 14 is lifted through the lift plate 17. At this time, the lifted diaphragm 14 moves the insertion portion 30a upward in the negative pressure creation passage 27. This creates a negative pressure state in the internal passage 23, allowing the expressed milk to flow into the temporary storage portion 26 from the inflow passage 25. When the temporary storage portion 26 is in a negative pressure state, the valve member 41 closes the bottom of the temporary storage portion 26, so that the milk flowing from the inflow passage 25 is stored in the temporary storage portion 26. That is, the valve member 41 allows the milk to be temporarily stored in the internal passage 23 of the breast pump 1 when the breast pump 1 is in a negative pressure state.

Specific operation of the valve body 43 is now described. When the handle 15 is not rotated in the direction of arrow D1, the internal passage 23 is in a normal pressure state, and the plate-shaped portion 57 of the valve member 41 is positioned adjacent to but separated from the partition wall 45 in the second space 47 as shown in FIG. 8. That is, a gap 61 is formed between the partition wall 45 and the first surface 57a.

As shown in FIG. 9, when the handle 15 is rotated in the direction of arrow D1 bringing the internal passage 23 into a negative pressure state, the plate-shaped portion 57 is warped, inserting parts of the plate-shaped portion 57 into the through-holes 53 in the direction from the second space 47 to the first space 46. This ensures that the through-holes 53 are closed. At this time, since the strength of the valve body 43 is enhanced by the annular protrusion 60 provided at the position corresponding to the through-holes 53, the valve body 43 is unlikely to be excessively warped toward the first space 46. The temporary storage portion 26 stores the milk flowing from the inflow passage 25. Since both the partition wall 45 and the plate-shaped portion 57 are molded products of an elastic synthetic resin material, they are brought into close contact with each other when the internal passage 23 is in a negative pressure state. This limits leakage of the milk stored in the temporary storage portion 26 through the through-holes 53.

Figure 10:
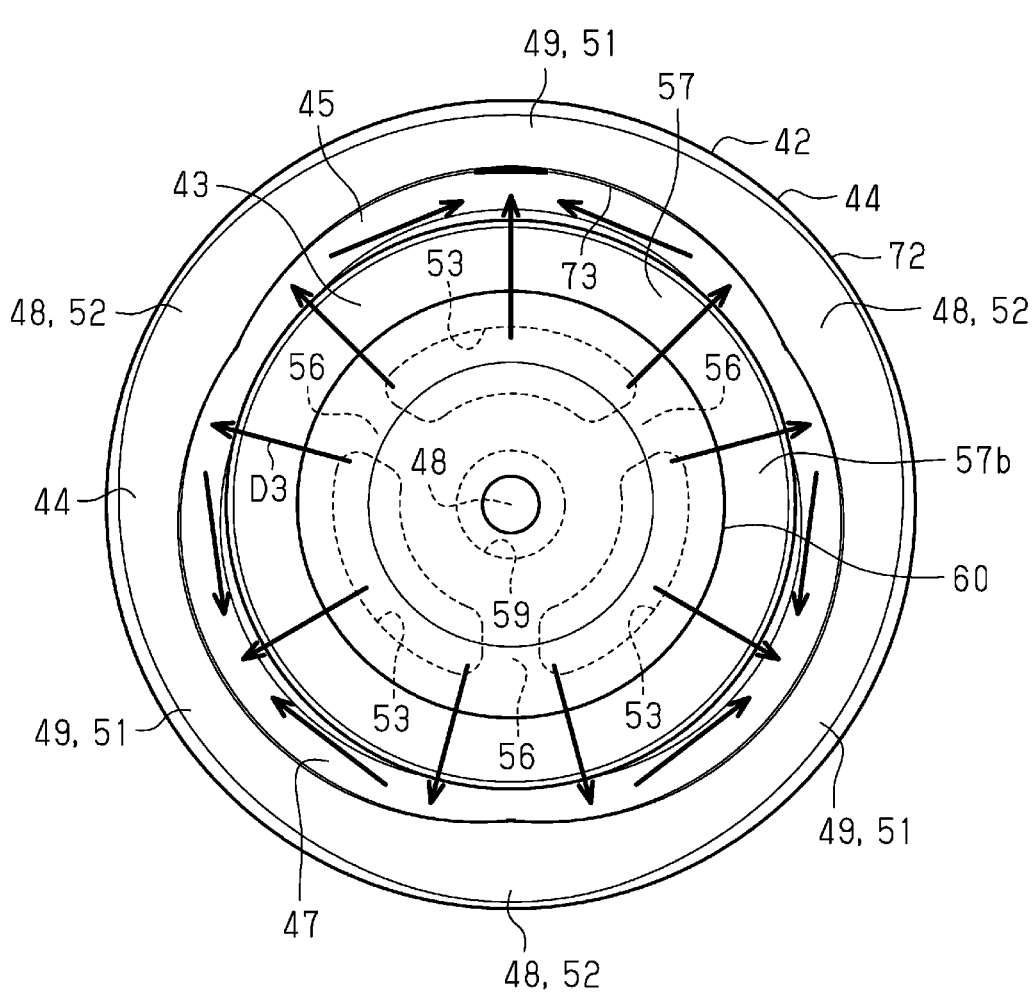
FIG. 10 is a bottom view of the cap in FIG. 8, showing flows of milk.

When the user loosens the grip on the handle 15, the elastic recovery of the diaphragm 14 rotates the handle 15 in the direction of arrow D2, returning the internal passage 23 to normal pressure. As a result, as shown in FIG. 8, the valve body 43 of the valve member 41 is relaxed relative to the partition wall 45 and brought into a state in which the valve body 43 is positioned adjacent to but separated from the partition wall 45 again. Then, as shown in FIG. 10, the milk stored in the temporary storage portion 26 flows down through the through-holes 53, is received by the plate-shaped portion 57, flows into the gap 61 between the partition wall 45 and the first surface 57a of the plate-shaped portion 57, and then flows outward in radial directions of the first surface 57a (the directions of arrows D3). That is, the valve member 41 is configured to allow the milk stored in the internal passage 23 to flow out when the breast pump 1 is in the normal pressure state. Specifically, the internal passage 23 is configured to connect the milk extraction opening 13c defined by the hood 13 to the bottle 12. While the breast pump 1 is in a negative pressure state created by the negative pressure creation mechanism, the valve member 41 allows the milk from the hood 13 to be temporarily stored in the internal passage 23. The valve member 41 is also configured to allow the milk stored in the internal passage 23 to flow out to the bottle 12 when the breast pump 1 is in a normal pressure state.

In the gap 57c between the outer circumference edge of the plate-shaped portion 57 and the inner surface 73 of the second outer circumference wall 72 defining the second space 47, a space is formed that is wider at positions corresponding to the thin sections 49 than at positions corresponding to the thick sections 48. That is, in the gap 57c between the outer circumference edge of the plate-shaped portion 57 and the inner surface 73 of the second outer circumference wall 72 defining the second space 47, a space is formed that is wider at positions corresponding to the through-holes 53 than at positions corresponding to the connection sections 56. Thus, some of the milk flowing down through the through-holes 53 and received by the plate-shaped portion 57 smoothly flows toward the thin sections 49 at positions corresponding to the through-holes 53. The remaining milk flows toward the thick sections 48. The milk flowing along the thin sections 49 flows toward the distal end portions (lower ends) of the high sections 51. The milk flowing along the thick sections 48 flows from the thick sections 48 to the thin sections 49. Then, most of the milk drips into the bottle 12 from the distal end portions (lower ends) of the high sections 51, which coincide with the thin sections 49. Some milk drips directly into the bottle 12 from the outer circumference edge of the plate-shaped portion 57.

Milk is extracted from the breast by repeatedly reciprocating the handle 15, and the insertion portion 30a also reciprocates in the negative pressure creation passage 27 in time with the reciprocating movement of the handle 15. As a result, a normal pressure state and a negative pressure state are repeatedly created in the internal passage 23. Thus, milk is successively stored in the temporary storage portion 26, and the milk stored in the temporary storage portion 26 drips into bottle 12.

After use, the breast pump 1 is disassembled as shown in FIG. 2 for cleaning. That is, the bottle 12, the hood 13, the handle 15, the handle base 16, the diaphragm 14, and the lift plate 17, to which the insertion portion 30a is attached, are removed from the main body 11. Then, the valve member 41 is also removed from the main body 11. The valve body 43 is separated from the cap 42 of the valve member 41. In this manner, the breast pump 1 can be easily assembled and disassembled and can be easily cleaned using fingers or a brush. By separating the cap 42 from the valve body 43, the components of the valve member 41 can also be easily cleaned using fingers or a brush. The cap 42 is free of small depressions, such as small through-holes and deep holes, facilitating cleaning of the first space 46, the second space 47, and the through-holes 53. The valve body 43 is also free of small depressions, facilitating cleaning of the valve body 43. After cleaning, the breast pump 1 is assembled as described above.

The breast pump 1 as described above has the following advantageous effects.

(1) By removing the valve body 43 from the cap 42 of the valve member 41, the valve member 41 can be easily cleaned. This allows the breast pump 1 to be kept clean.

(2) The operation of attaching or detaching the valve body 43 with respect to the cap 42 only involves attachment or detachment of the attachment projection 58 with respect to the attachment hole 59, and is thus easy.

(3) The milk flowing out through the through-holes 53 into the second space 47 is received by the plate-shaped portion 57 of the valve member 41 and then flows toward the outer circumference wall 44. The space inside the outer circumference wall 44 subsequent to the through-holes 53 is wider at positions corresponding to the thin sections 49 than at positions corresponding to the thick sections 48. Thus, the milk flowing out through the through-holes 53 and received by the plate-shaped portion 57 tends to flow toward the thin sections 49 of the outer circumference wall 44. Some of the milk is transferred from the outer circumference edge of the valve body 43 to the thick sections 48 and the thin sections 49 and flows into the bottle 12 from the distal end of the outer circumference wall 44. Thus, the flow of some of the milk is conditioned and moves into the bottle 12 from the distal end (lower end) of the second outer circumference wall 72 defining the second space 47. Thus, as compared to a configuration in which the milk is scattered into the bottle, the dripping sound is reduced.

(4) Some of the milk that flows out through the through-holes 53, is received by the plate-shaped portion 57, and flows to the outer circumference wall 44 is then guided from the low sections 52 of the thick sections 48 to the high sections 51 of the thin sections 49. Then, the milk tends to flow into the bottle 12 from the distal end portions of the high sections 51. Since the distance from the high sections 51 to the liquid surface in the bottle 12 is less than the distance from the low sections 52 to the liquid surface in bottle 12, the greater the amount of milk dripping from high sections 51, the lower the dripping sound becomes.

(5) The portion of the outer circumference wall 44 defining the second space 47 includes the low sections 52 having the second height H2. Providing the low sections 52 of the second height H2 reduces the amount of elastic synthetic resin material used for the outer circumference wall 44, as compared to a configuration in which the outer circumference wall only has the first height H1 and is formed by the high sections 51 of the uniform height, for example.

(6) Between the inner surface 73 of the outer circumference wall 44 and the valve body 43, a space is formed that is wider at positions corresponding to the thin sections 49, which are formed at positions corresponding to the through-holes 53, than at positions corresponding to the thick sections 48, which are formed at positions corresponding to the connection sections 56. As such, some of the milk flowing out through the through-holes 53 tends to flow along the thin sections 49. Some of the milk is transferred from the outer circumference edge of the valve body 43 to the thick sections 48 and the thin sections 49, and most of the milk flows into the bottle 12 from the distal end portion of the outer circumference wall 44.

(7) A negative pressure state of the temporary storage portion 26 brings the valve body 43 into close contact with the partition wall 45, so that the through-holes 53 are firmly closed.

(8) The first surface 57a serving as the facing surface facing the partition wall 45 is frosted, reducing the likelihood of the first surface 57a sticking to the partition wall 45. The above embodiment may be modified as follows.

The frosted first surface 57a of the plate-shaped portion 57 is unlikely to stick to the partition wall 45. The surface of the attachment projection 58 does not necessarily have to be frosted. It is sufficient that at least the sections of the first surface 57a that face the connection sections 56 of the partition wall 45 are frosted.

The valve body 43 of the valve member 41 may be a molded product of any elastic synthetic resin material. The valve body 43 does not have to include the same elastic synthetic resin material as the cap 42. Also, the cap 42 may be a molded product of a synthetic resin material having a higher rigidity than the valve body 43. This is because the valve body 43 only needs to close the through-holes 53.

The number of through-holes 53 may be one, two, or four or more. For example, a large number of through-holes 53 forming parts of a perfect circle or parts of an elliptical shape may be provided around the attachment hole 59 in a scattered manner. Also, the shape of each through-hole is not limited to an elongated hole having an arcuate shape. The through-holes 53 may be straight elongated holes extending in the radial directions, for example.

The thick sections 48 may be provided at the positions of the through-holes 53, and the thin sections 49 may be provided at the positions of the connection sections 56.

The second outer circumference wall 72 defining the second space 47 does not have to include both the high sections 51 and the low sections 52. In an example, the height of the second outer circumference wall 72 from the partition wall 45 may be uniformly set to the first height H1, which is the height of the high sections 51. This reduces the dripping sound. Conversely, the height of the second outer circumference wall 72 from the partition wall 45 may be uniformly set to the second height H2 of the low section 52. This reduces the amount of synthetic resin material used. When the height of the second outer circumference wall 72 defining the second space 47 is uniform, the structure of the outer circumference wall 44 is simplified.

The outer circumference wall 44 does not have to include the thick sections 48 and the thin sections 49, and may have a uniform thickness. For example, provided that the strength of the outer circumference wall 44 is ensured, the outer circumference wall 44 may uniformly have the second thickness T2 of the thin sections 49. This reduces the amount of synthetic resin material used. Conversely, the outer circumference wall 44 may uniformly have the first thickness T1 of the thick sections 48.

The attachment structure of the valve body 43 to the cap 42 is not limited to the above example. In one example, the valve body 43 may include an attachment hole at its center, and the surface of the partition wall 45 facing the second space 47 may include the attachment projection 58 at its center. Alternatively, the outer circumference portion of the surface of the partition wall 45 facing the second space 47 may include one of a set of attachment projections 58 and a set of attachment holes 59 at regular intervals. The valve body 43 may include the other of a set of attachment projections 58 and a set of attachment holes 59 as the counterpart for the partition wall 45.

To reduce the number of components, the lift plate 17 and the insertion member 30 may be formed as one component that is integrally molded. Also, the insertion member 30 may be omitted as long as the negative pressure creation mechanism using the diaphragm 14 is maintained. Additionally, the lift plate 17 may be omitted, and the connection projection 32 as a connection portion to be connected to the lift portion 37 of the handle 15 may be provided on the outer surface of the diaphragm 14.

The handle 15 may be directly supported by the main body 11 in a rotational manner, instead of being supported through the handle base 16. In this case, the rotation support piece 35 and the support shaft portion 36 are formed integrally with the main body 11.

The bottle 12 does not have to be attachable and detachable with respect to the bottle attachment portion 21, and the bottle 12 may be integral with the bottle attachment portion 21. Also, the hood 13 does not have to be attachable and detachable with respect to the hood attachment portion 22, and the hood 13 may be integral with the hood attachment portion 22. The storage container may a flexible bag, instead of the bottle 12.

The breast pump 1 to which the valve member 41 is applied is not limited to a manual configuration as described above. The valve member 41 is applicable to electric breast pumps.

As used herein, the phrase "at least one of A and B" should be understood to refer to "only A", "only B", or "both A and B."

The invention claimed is:

1. A valve member for a breast pump, the valve member being configured to allow milk to be temporarily stored in an internal passage when the breast pump is in a negative pressure state, and to allow the milk stored in the internal passage to flow out when the breast pump is in a normal pressure state, the valve member comprising:

a cap configured to be attached to the breast pump, the cap including a partition wall separating a first space on an inflow side of the milk from a second space on an outflow side of the milk, and a through-hole disposed in the partition wall to connect the first space to the second space, wherein the cap includes an outer circumference wall, and wherein a portion of the outer circumference wall defining the second space includes a thick section that has a first thickness and bulges inward and a thin section that is thinner than the thick section and has a second thickness; and a valve body disposed in the second space, the valve body being configured to close the through-hole when the negative pressure state is created, and to open the through-hole when the normal pressure state is established.

2. The valve member according to claim 1, wherein the valve body includes a plate-shaped portion for closing the through-hole, and an attachment projection extending from the plate-shaped portion, and wherein the partition wall includes an attachment hole that is engaged with the attachment projection.

3. The valve member according to claim 1, wherein the portion of the outer circumference wall defining the second space includes a high section that has a first height as a height from the partition wall, and a low section that has a second height as a height from the partition wall, the second height being lower than the first height, and wherein the thick section is formed in the low section, and the thin section is formed in the high section.

4. The valve member according to claim 1, wherein the through-hole is one of a plurality of through-holes arranged in the partition wall in a circumferential direction, wherein the partition wall includes a central region inward of the through-holes, an outer circumference region radially outward of the through-holes, and a plurality of connection sections disposed between adjacent ones of the through-holes to connect the central region to the outer circumference region, wherein the thick section is one of a plurality of thick sections, and the thin section is one of a plurality of thin sections, and wherein in the portion of the outer circumference wall defining the second space, the thick sections are disposed at positions corresponding to the connection sections, and the thin sections are disposed at positions corresponding to the through-holes.

5. The valve member according to claim 1, wherein the valve body is a molded product of an elastic synthetic resin material.

6. The valve member according to claim 1, wherein the valve body includes a plate-shaped portion for closing the through-hole, and wherein the plate-shaped portion has a facing surface that faces the partition wall and is frosted.

7. A breast pump comprising:

a storage container configured to store milk;

a hood configured to be applied to a breast;

an internal passage configured to temporarily store expressed milk and to connect a milk extraction opening defined by the hood to the storage container;

a valve member configured to cause the milk temporarily stored in the internal passage to flow out to the storage container; and a negative pressure creation mechanism configured to alternately create a negative pressure state and a normal pressure state in the internal passage, wherein the valve member is configured to allow milk from the hood to be temporarily stored in the internal passage when the breast pump is in the negative pressure state, and to allow the milk stored in the internal passage to flow out to the storage container when the breast pump is in the normal pressure state, and wherein the valve member includes:

a cap configured to be attached to the breast pump, the cap including a partition wall separating a first space on an inflow side of the milk from a second space on an outflow side of the milk, and a through-hole disposed in the partition wall to connect the first space to the second space, wherein the cap includes an outer circumference wall, and wherein a portion of the outer circumference wall defining the second space includes a thick section that has a first thickness and bulges inward and a thin section that is thinner than the thick section and has a second thickness; and a valve body disposed in the second space, the valve body being configured to close the through-hole when the negative pressure state is created, and to open the through-hole when the normal pressure state is established.

8. A breast pump comprising:

a storage container configured to store milk;

a hood configured to be applied to a breast;

an internal passage configured to temporarily store expressed milk and to connect a milk extraction opening defined by the hood to the storage container;

a valve member configured to cause the milk temporarily stored in the internal passage to flow out to the storage container; and a negative pressure creation mechanism configured to alternately create a negative pressure state and a normal pressure state in the internal passage, wherein the valve member is configured to allow milk from the hood to be temporarily stored in the internal passage when the breast pump is in the negative pressure state, and to allow the milk stored in the internal passage to flow out to the storage container when the breast pump is in the normal pressure state, and wherein the valve member includes:

a cap attached to the breast pump, the cap including a partition wall separating a first space on an inflow side of the milk from a second space on an outflow side of the milk, and a through-hole disposed in the partition wall to connect the first space to the second space, wherein the cap includes an outer circumference wall, and wherein a portion of the outer circumference wall defining the second space includes a thick section that has a first thickness and bulges inward and a thin section that is thinner than the thick section and has a second thickness; and a valve body disposed in the second space, the valve body being configured to close the through-hole when the negative pressure state is created, and to open the through-hole when the normal pressure state is established, wherein the valve body includes a plate-shaped portion for closing the through-hole, and an attachment projection extending from the plate-shaped portion, and wherein the partition wall includes an attachment hole that is engaged with the attachment projection.

9. The breast pump according to claim 7, wherein the valve body includes a plate-shaped portion for closing the through-hole, and an attachment projection extending from the plate-shaped portion, and wherein the partition wall includes an attachment hole that is engaged with the attachment projection.

10. The breast pump according to claim 7, wherein the portion of the outer circumference wall defining the second space includes a high section that has a first height as a height from the partition wall, and a low section that has a second height as a height from the partition wall, the second height being lower than the first height, and wherein the thick section is formed in the low section, and the thin section is formed in the high section.

11. The breast pump according to claim 7, wherein the through-hole is one of a plurality of through-holes arranged in the partition wall in a circumferential direction, and wherein the partition wall includes a central region inward of the through-holes, an outer circumference region radially outward of the through-holes, and a plurality of connection sections disposed between adjacent ones of the through-holes to connect the central region to the outer circumference region.

12. The breast pump according to claim 11, wherein the thick section is one of a plurality of thick sections, and the thin section is one of a plurality of thin sections, and wherein in the portion of the outer circumference wall defining the second space, the thick sections are disposed at positions corresponding to the connection sections, and the thin sections are disposed at positions corresponding to the through-holes.

13. The breast pump according to claim 7, wherein the valve body is a molded product of an elastic synthetic resin material.

14. The breast pump according to claim 7, wherein the valve body includes a plate-shaped portion for closing the through-hole, and wherein the plate-shaped portion has a facing surface that faces the partition wall and is frosted.

15. The breast pump according to claim 8, wherein the plate-shaped portion has a facing surface that faces the partition wall and is frosted.

16. The breast pump according to claim 8, wherein the valve body is a molded product of an elastic synthetic resin material.

17. The breast pump according to claim 8, wherein the portion of the outer circumference wall defining the second space includes a high section that has a first height as a height from the partition wall, and a low section that has a second height as a height from the partition wall, the second height being lower than the first height, and wherein the thick sections is formed in the low section, and the thin section is formed in the high section.

18. The breast pump according to claim 17, wherein the through-hole is one of a plurality of through-holes arranged in the partition wall in a circumferential direction, wherein the partition wall includes a central region inward of the through-holes, an outer circumference region radially outward of the through-holes, and a plurality of connection sections disposed between adjacent ones of the through-holes to connect the central region to the outer circumference region, wherein the thick section is one of a plurality of thick sections, and the thin section is one of a plurality of thin sections, and wherein in the portion of the outer circumference wall defining the second space, the thick sections are disposed at positions corresponding to the connection sections, and the thin sections are disposed at positions corresponding to the through-holes.

\* \* \* \* \*